United States Patent [19]

Andersson et al.

[11] Patent Number: 4,798,595
[45] Date of Patent: Jan. 17, 1989

[54] INJECTION DEVICE

[76] Inventors: Ingvar Andersson, Pl 80, S-450 34 Fiskebäckskil; Jan Wadstein, Jaktvarvsvägen, S-133 00 Slatsjöbaden, both of Sweden

[21] Appl. No.: 51,958
[22] PCT Filed: Sep. 9, 1986
[86] PCT No.: PCT/SE86/00396
§ 371 Date: Apr. 29, 1987
§ 102(e) Date: Apr. 29, 1987
[87] PCT Pub. No.: WO87/01292
PCT Pub. Date: Mar. 12, 1987
[51] Int. Cl.⁴ .............................................. A61M 5/32
[52] U.S. Cl. ......................... 604/174; 128/DIG. 26; 604/274
[58] Field of Search ............... 604/22, 27, 28, 51, 604/93, 174, 175, 239, 240, 272–274, 173; 128/DIG. 6, DIG. 26, 335, 337, 339

[56] References Cited
U.S. PATENT DOCUMENTS

| | | | |
|---|---|---|---|
| 1,549,565 | 8/1925 | Stadler | 604/130 |
| 2,336,689 | 12/1943 | Karle | 128/339 |
| 2,989,053 | 6/1961 | Hamilton | 604/411 |
| 3,021,842 | 2/1962 | Flood | 604/175 |
| 3,509,880 | 5/1970 | Guttman | 604/274 |
| 3,825,010 | 7/1974 | McDonald | 604/174 |
| 4,317,451 | 3/1982 | Cerwin et al. | 128/335 |
| 4,345,601 | 8/1982 | Fukuda | 128/339 |
| 4,403,987 | 9/1983 | Gottinger | 604/115 |
| 4,531,522 | 7/1985 | Bedi et al. | 128/335 |
| 4,559,039 | 12/1985 | Ash et al. | 604/175 |
| 4,676,245 | 6/1987 | Fukuda | 128/335 |

Primary Examiner—Dalton L. Truluck
Attorney, Agent, or Firm—Albert L. Jeffers

[57] ABSTRACT

The present invention relates to an injection arrangement. This is characterized in that it comprises an injection needle (1) and a base plate (8). The needle (1) is curved so that at least one part of it exhibits a circular arc with a certain radius of curvature. The needle (1) is executed at one end with a solid, cutting point (2). The needle (1) has a central duct (3) which is closed in the area ahead of the tip (2) of the needle, and along the area in the form of a circular arc it has a number of openings (6) communicating with the duct (3). The base plate (8) has two curved ducts (11,12) passing through the plate (8) at an angle to one another and with the same radius of curvature as the needle (1). The base plate (8) also supports a cradle (13), to which the needle (1) is attached, which cradle is able to move in the base plate in such a way that the needle (1) is able to move in a normal plane to the plane of the base plate (8) in a reciprocating fashion about the center of the radius of curvature. During forward movement of this kind, the tip (2) of the needle (1) moves from a first end position down through the first curved duct (11) and then up through the second duct (12) to a second end position.

2 Claims, 6 Drawing Sheets

FIG 4c
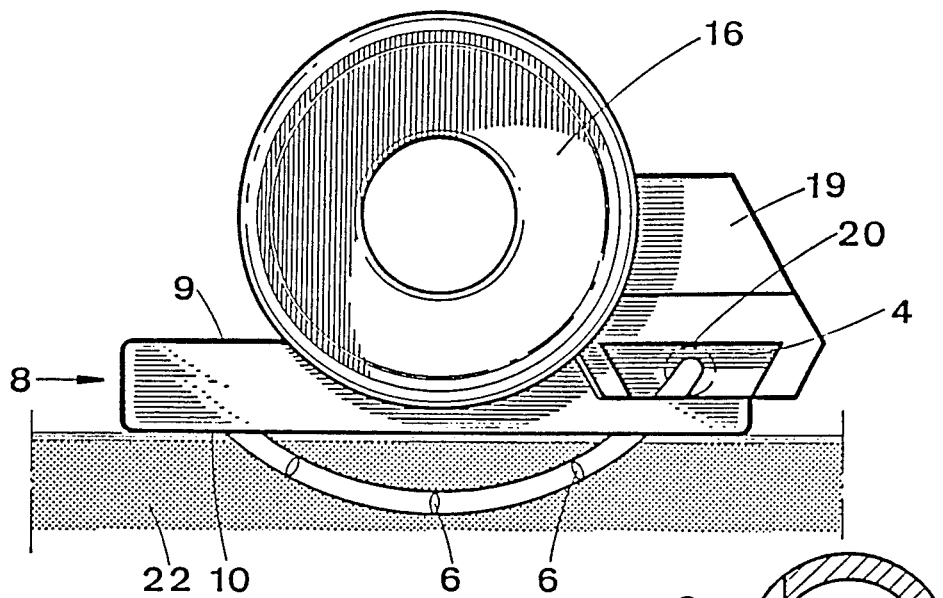
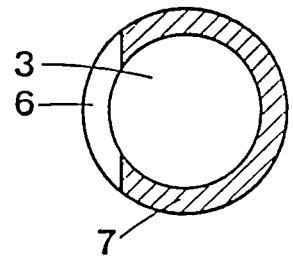
FIG 2
FIG 5
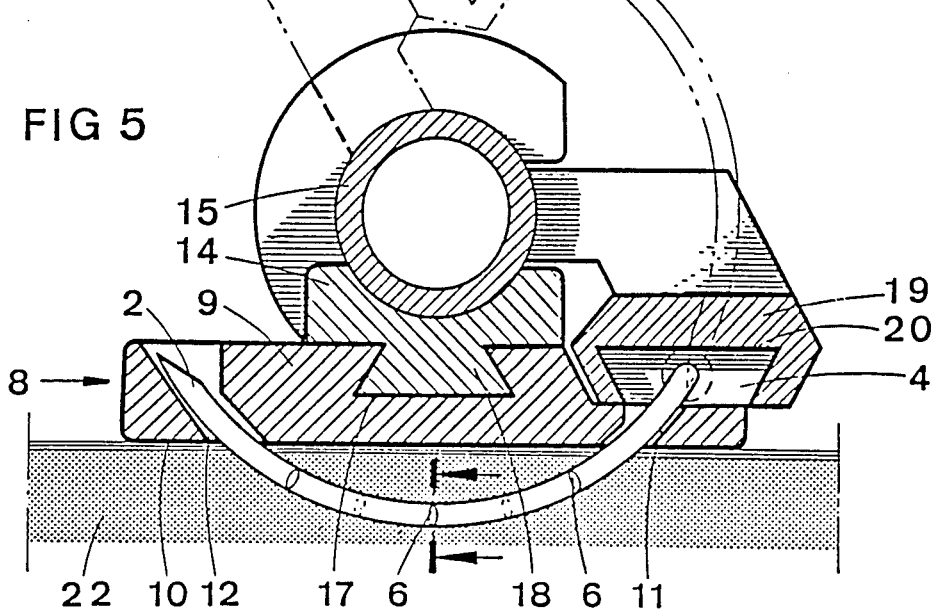

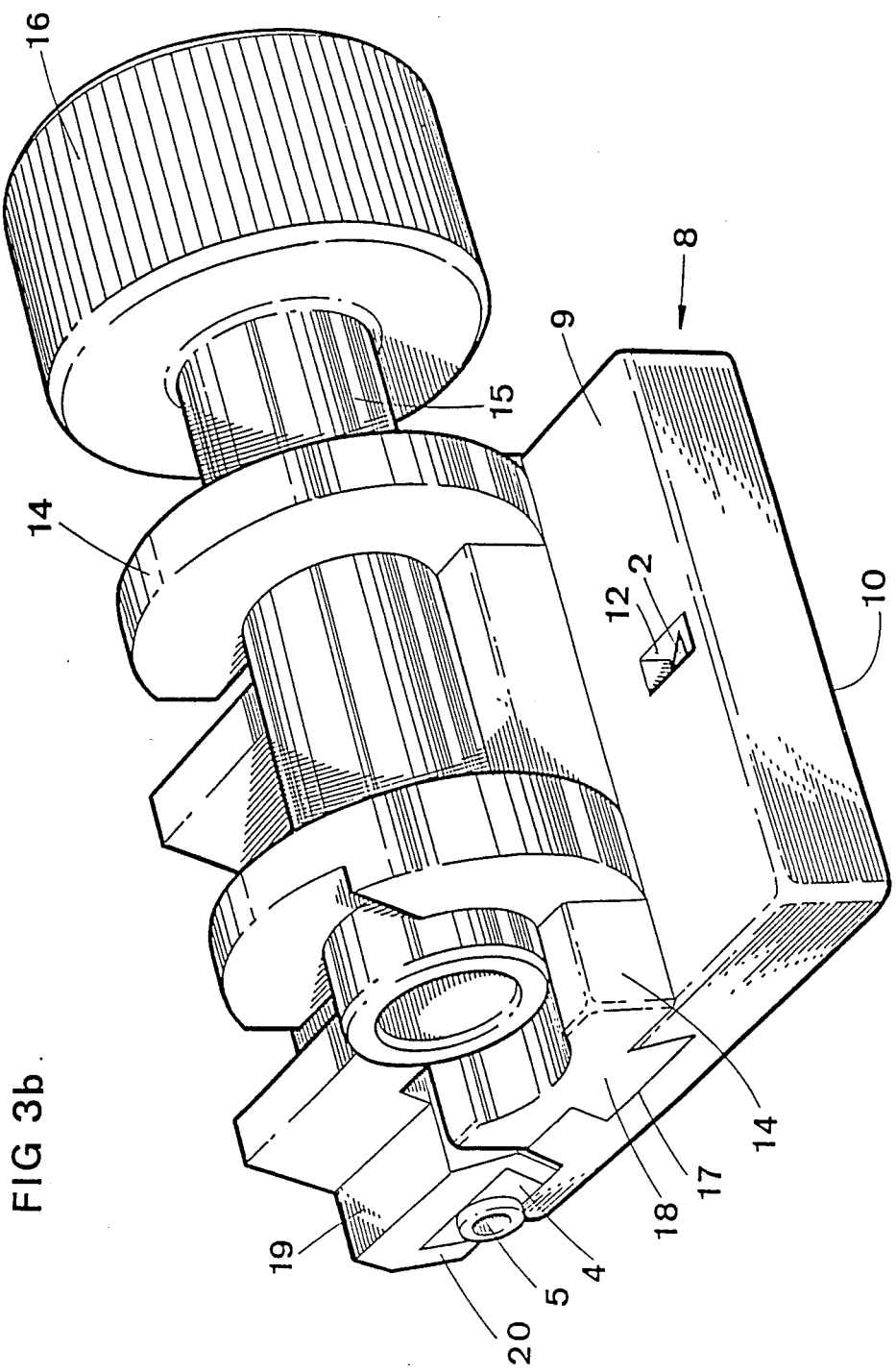

INJECTION DEVICE

The present invention relates to an injection arrangement.

During injection with a conventional needle, the needle is introduced through the skin into the area of the tissue where the drug is to be deposited. In the case of subcutaneous injections (in the subcutaneous area) the fat cells are torn apart, leading to subsequent chemical inflammation. Furthermore a conventional needle, when used as an in situ needle for the continuous or repeated administration of drugs, suffers from the disadvantage that the tip of the needle is not securely anchored, but is able as a result of vertical and lateral movements to destroy surrounding cells. Fats are released in conjunction with the destruction of fat cells, and this in turn leads to inflammatory reactions around the tip of the needle. If a catheter, for example a subcutaneous catheter made of a plastics material, is used instead, the risk of infection will be created when the insertion sleeve passes down into underlying tissue.

In conjunction with injections performed by means of previously disclosed injection arrangements, the entire dose of the drug is deposited at the tip of the needle. A number of drugs have an irritative effect, in particular if the drug is deposited in a large quantity.

The object of the present invention is to make available an injection arrangement in which the above-mentioned disadvantages have been eliminated or at least reduced, and by means of which the injection can be performed with great accuracy with regard to the depth of the injection. This is achieved in accordance with the invention in that the arrangement comprises an injection needle which is curved so that at least one part of it exhibits a circular art with a certain radius of curvature, and which is executed at one end with a solid, cutting tip, has a central duct which is closed in the area ahead of the tip of the needle, and along the area in the form of a circular arc has a number of openings communicating with the duct, and a base plate in which there are present two curved ducts passing through the plate at an angle to one another and with the same radius of curvature as the needle, in that the base plate supports a cradle, to which the needle is attached, and in that the needle is able to move in a normal plane to the plane of the base plate in a reciprocating fashion about the centre of the radius of curvature, in conjunction with which, during forward movement of this kind, the tip of the needle moves from a first end position down through the first curved duct and then up through the second duct to a second end position.

A cutting tip on straight injection needles is previously disclosed in, for example, U.S. Pat. Nos. 2,989,053 and 3,509,880. In conjunction with the insertion of the needle, the cutting tip causes less irritation and less destruction of cells than is the case with conventional injection needles. The fact that the drug is distributed through a number of holes results in the advantage that it is distributed over a larger area, which not only facilitates the resorption of the drug in question, but also reduces the quantity of the drug at a given point and with it the risk of irritations.

As the needle is inserted, the tip of the needle penetrates the skin twice and is secured above the area of the skin. This means reduced destruction of cell tissue and less pain, since the needle is securely anchored with its tip outside the tissue. The fact that the needle is secured also reduces the risk of infections at the point of entry by the needle. The possibility is thus afforded of leaving the needle in place for a considerably longer period than is the case with previously disclosed injection arrangements, which is of major importance to, for example, diabetics and long-term care patients.

BRIEF DESCRIPTION OF THE DRAWING

The invention is described below in more detail with reference to the accompanying drawing, in which

FIG. 2 shows a cross section through the needle in FIG. 1.

FIG. 3a and 3b show a perspective view seen from above of an illustrative embodiment of an arrangement in accordance with the invention, with the needle in an initial position and in an inserted position respectively.

FIGS. 4a, 4b and 4c are plan views respectively from one side, from above, and from a second side which forms a right angle with the first-mentioned side, of the arrangement in accordance with FIG. 3b, that is to say with the needle in the inserted position.

FIG. 5 is a cross section through the arrangement in accordance with the invention, as illustrated in FIG. 4.

Figure 1:
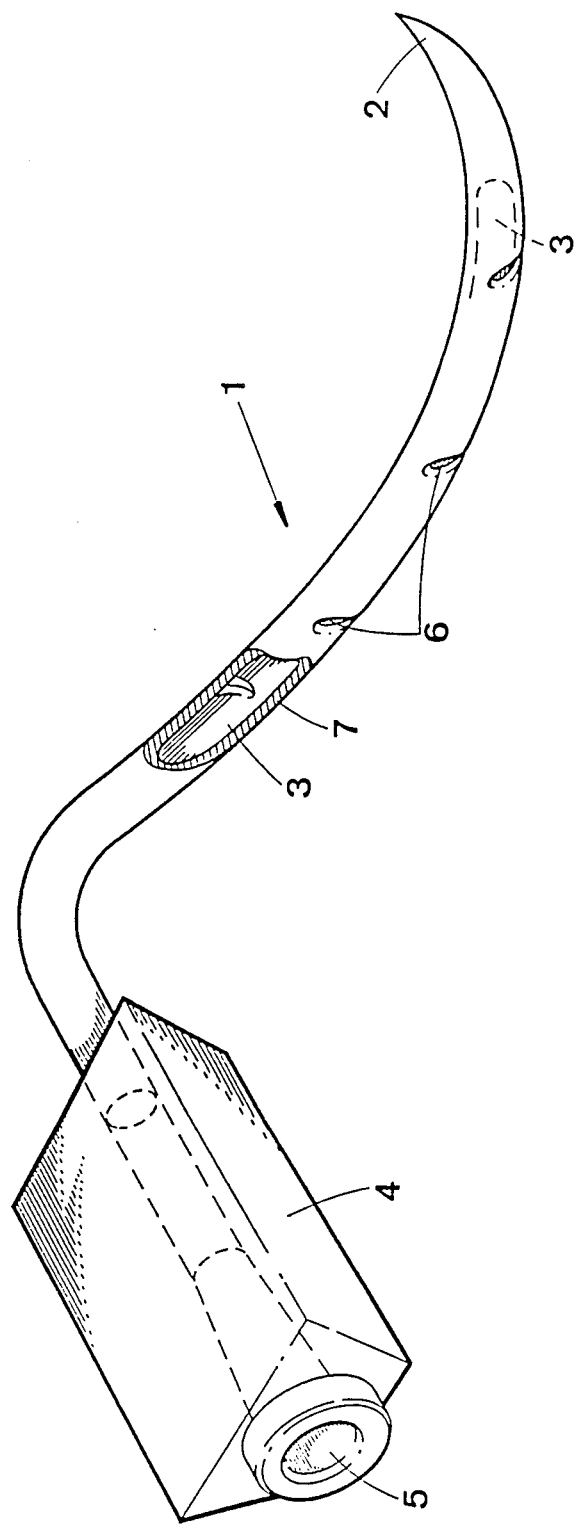
FIG. 1 shows in perspective view an illustrative embodiment of an injection needle in an arrangement in accordance with the invention.

An injection arrangement in accordance with the present invention comprises an injection needle 1 and devices for inserting and withdrawing same. The needle 1 is executed at one end with a cutting tip 2 and has a central duct 3. The other end of the needle 1 is attached to a body 4, preferably consisting of a plastics material, executed with a bore 5 which communicates with the duct 3. The bore is preferably in the form of a cone, a so-called luer cone, and is designed to fit the corresponding conical shape of an injection syringe so as to connect the latter to the injection needle 1. The external form of the body 4 will be described below.

The duct 3 is closed in the area ahead of the tip 2 of the needle, that is to say the actual tip of the needle is solid. At least one part of the needle 1 is also curved so as to form a circular arc with a certain radius of curvature. Along the area of the needle 1 which is in the form of a circular arc there are arranged a number of openings 6 communicating with the duct 3, through which openings a drug can be deposited. These openings may be produced by, for example, cylindrical milling into the wall 7 of the needle, as shown in FIG. 2. As has already been mentioned, the drug will be distributed in this way over a larger area than is the case for injections using a conventional needle, which means that there is a reduced risk of irritations and facilitates the resorption of the drug.

Although the needle in accordance with the present invention itself possesses the above advantages, additional advantages can be gained by means of devices for inserting and withdrawing the needle, such as simplified insertion and the possibility of leaving the needle in postion for quite a lengthy period without causing irritation.

The aforementioned insertion and withdrawal devices for the needle 1 consist of a base plate 8, preferably made of a plastics material, which is of rectangular form in the embodiment illustrated in the drawing, but which can also be circular or oval, for example. Running between the upper and lower surfaces 9 and 10 of the base plate 8 are two curved ducts 11, 12 arranged at an angle to one another and with a common centre of curvature and the same radius of curvature as the area of the needle 1 which is in the form of a circular arc.

Figure 3A:
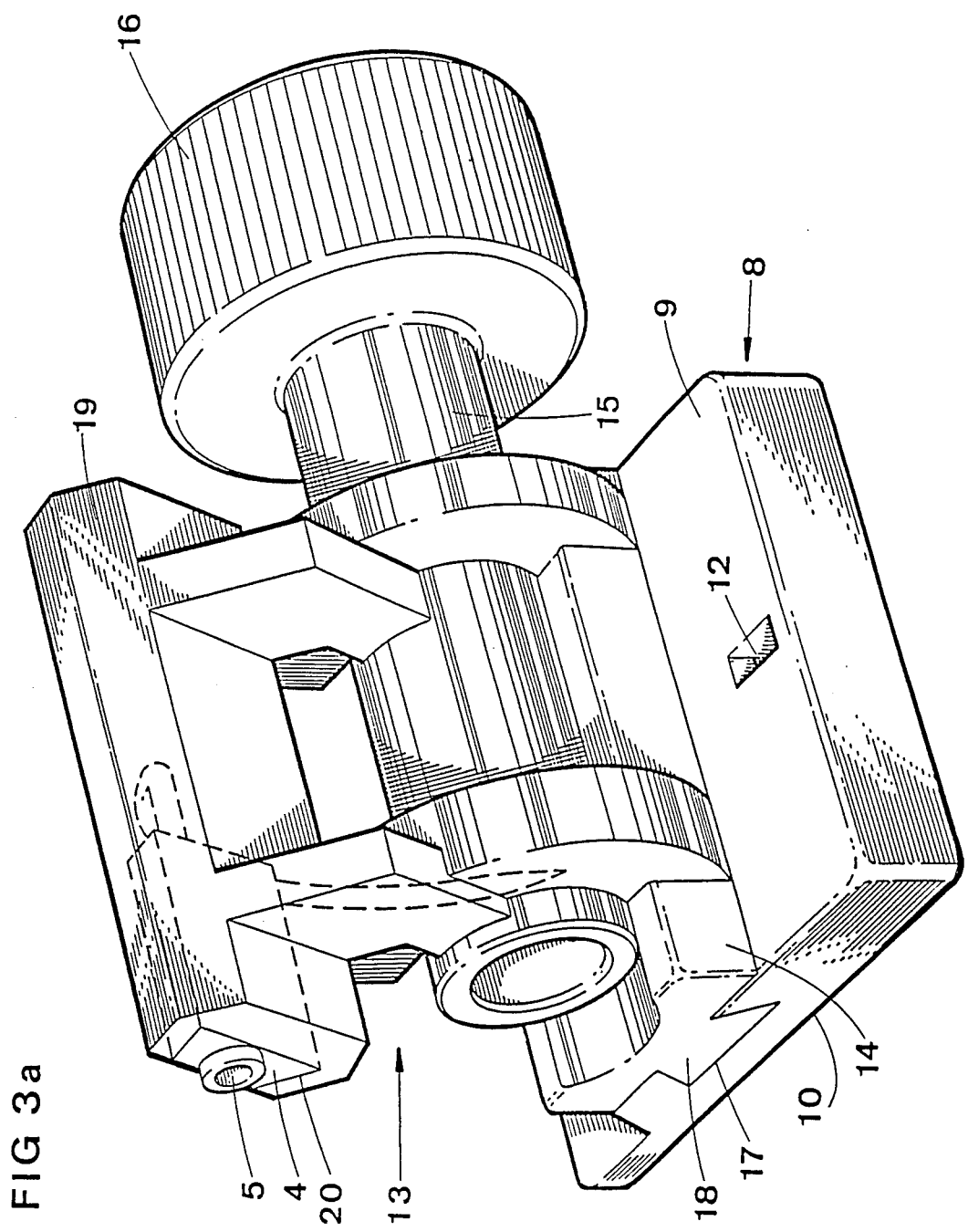
Figure 4A:
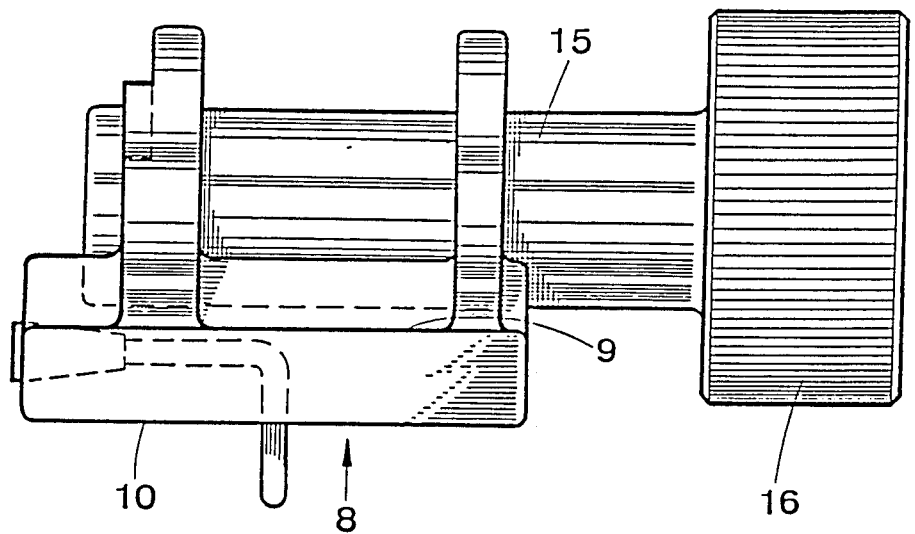

The base plate 8 supports a cradle 13 which comprises a base component 14 having a shaft 15 pivotally mounted in it, which shaft is so executed at one end as to exhibit a wheel 16 to facilitate the manual rotation of the shaft. In order to be able to attach the base component 14 to the base plate 8 in a detachable fashion, the base plate is provided in the embodiment illustrated in the drawing with a dovetail 17, and the base component is executed with a corresponding dovetail slot 18. Arranged on the shaft 15, the centre line of which passes through the aforementioned centre of curvature of the ducts 11 and 12, is a holder component 19, which is so executed as to hold the needle 1 in a position such that the centre of curvature of its section which is in the form of a circular arc coincides with that of the ducts 11, 12. By rotating the shaft 15, the needle is caused to describe a rotating motion in a normal plane to the base plate 8, in conjunction with which its tip 2 initially moves down from a first end position through the duct 11 and then moves up through the duct 12 to a second end position. The first end position for the tip 2 of the needle is shown in FIG. 3a, and with a dotted and dashed line in FIG. 5. The second end position is illustrated in FIGS. 3b, 4a, b and c, and in FIG. 5. For the purpose of securing the needle in the holder component 19, the latter is executed in the embodiment illustrated in the drawing with a dovetail slot 20, and the body 4 is designed in such a way that it forms the tongue of the dovetail 20. It is obvious that the aforementioned detachable connections between the base component 14 of the cradle 13 and the base plate 8, and between the holder component 19 and the body 4 can be executed in many other ways than that illustrated in the drawing.

Figure 4B:
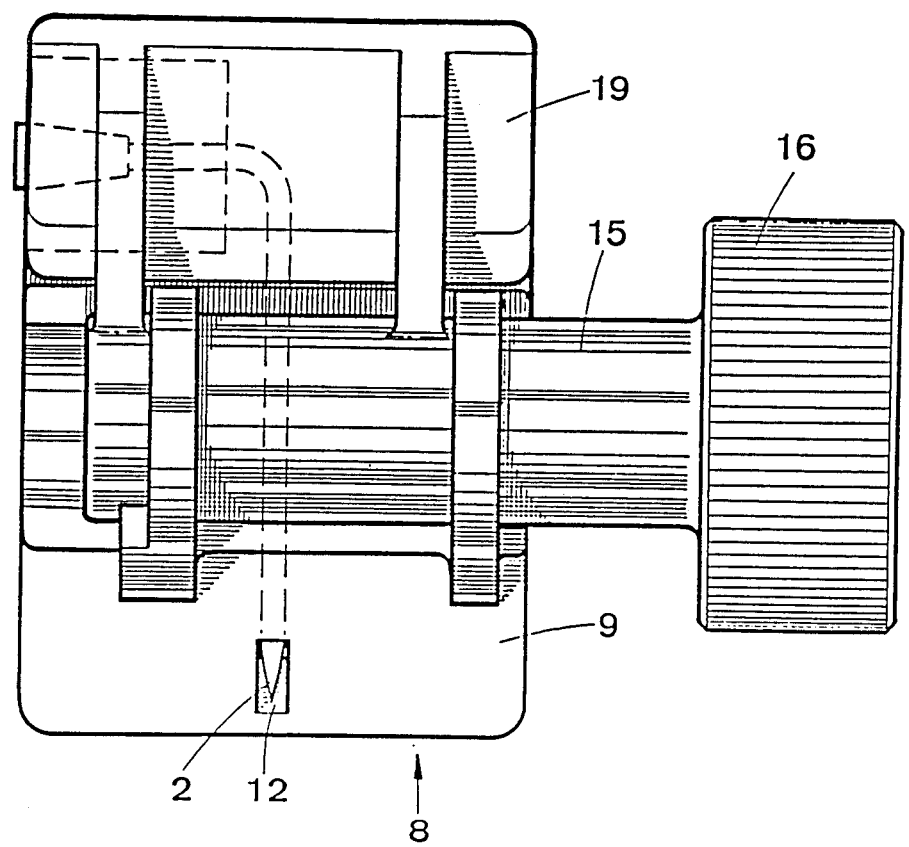
Figure 6:
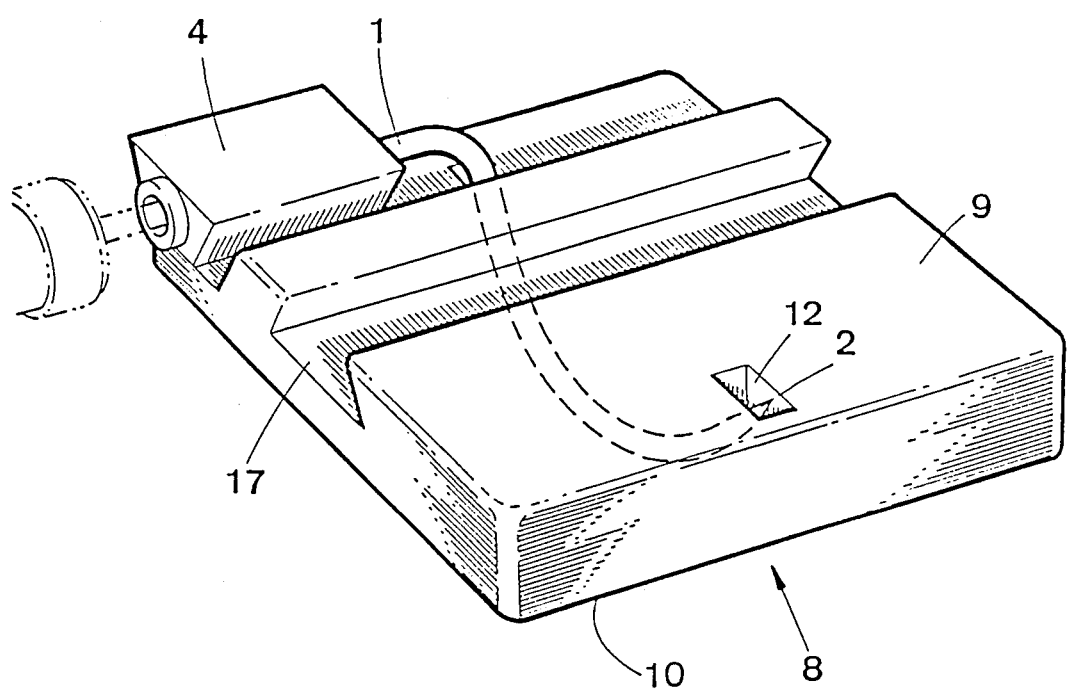
FIG. 6 shows the arrangement in accordance with the invention in its state after the needle has been inserted for a period of several days.

The use of the needle in accordance with the invention is facilitated by the aforementioned insertion and withdrawal devices, although the needle can, of course, be used separately. In order to facilitate the reader's understanding of the principle involved, an insertion procedure is now described with reference to the drawing, for which purpose it is assumed that the injection arrangement is adapted in the manner illustrated in FIG. 3a. The tip 2 of the needle is in its first end position here. The base plate 8 is placed on the skin at the point where insertion is to take place. The wheel 16 is rotated rapidly, causing the tip 2 of the needle to move down through the duct 11, through the skin, which is marked as a grid pattern and by the number 22 in FIGS. 4 and 5, and up through the duct 12 into its second end position, which is illustrated in FIG. 5. The cradle 13 can now be removed, so that the base plate 8 and the needle 1 with the body 4 are all that remain of the injection arrangement; see FIG. 6. Withdrawal of the needle is effected in the reverse sequence to that of insertion.

We claim:

1. An injection arrangement comprising an injection needle which is curved so that at least one part of it is shaped in a circular arc with a certain radius of curvature, said needle having a solid cutting tip and a central duct extending therethrough to said solid cutting tip, said needle having a plurality of openings on the circular arc shaped part communicating with the duct;
    a base plate having two curved ducts passing through the plate at an angle to one another with the same radius of curvature as the needle;
    a cradle supported by the base plate, to which the needle is attached, said cradle having the ability to move in the base plate in such a way that the needle is able to move in a normal plane to the plane of the base plate in a reciprocating fashion about the center of the radius of curvature, whereby during forward movement, the tip of the needle moves from a first end position down through the first curved duct and then up through the second duct to a second end position.

2. An arrangement according to patent claim 1, characterized in that the arrangement contains devices so arranged as to secure the needle in a detachable fashion in at least one of the aforementioned positions.

* * * * *